United States Patent
Meyerhoff et al.

(10) Patent No.: US 6,469,049 B1
(45) Date of Patent: Oct. 22, 2002

(54) METHOD OF TREATING, PREVENTING OR INHIBITING CENTRAL NERVOUS SYSTEM INJURIES AND DISEASES

(75) Inventors: James L. Meyerhoff, Silver Spring, MD (US); Debra L. Yourick, Linthicum Heights, MD (US); Michael L. Koenig, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/839,905

(22) Filed: Apr. 20, 2001

Related U.S. Application Data
(60) Provisional application No. 60/198,958, filed on Apr. 21, 2000.

(51) Int. Cl.[7] .................. A01N 43/26; A01N 37/00; A61K 31/385; A61K 31/19

(52) U.S. Cl. ..................... 514/440; 514/557

(58) Field of Search .................. 514/440, 557

(56) References Cited

U.S. PATENT DOCUMENTS

| | | | | |
|---|---|---|---|---|
| 5,084,481 A | * | 1/1992 | Ulrich et al. | 514/557 |
| 5,569,570 A | * | 10/1996 | Weischer et al. | 514/440 |
| 5,977,162 A | * | 11/1999 | Seidman | 514/440 |
| 6,197,340 B1 | | 3/2001 | Byrd et al. | 424/468 |

FOREIGN PATENT DOCUMENTS

| WO | WO 00/64440 | 11/2000 |
|---|---|---|
| WO | WO 00/74672 A1 | 12/2000 |

OTHER PUBLICATIONS

Willmore et al. (1978) Brain Research vol. 152 pp. 406–410.*
Willmore et al. (1982) Brain Research vol. 246 pp. 113–119.*
Willmore et al. (1983) Brain Research vol. 277 pp. 393–396.*
Willmore et al. (1981) Neurology vol. 31 pp. 63–69.*
Engstrom et al. (2000) Epilepsy Research vol. 43, pp. 135–144.
Willmore et al. (1978) Science vol. 200, pp. 1501–1503.
Willmore et al. (1978) Ann. Neurology vol. 4, pp. 329–336.
Willmore et al. (1989) Int. J. Devl. Neuroscience vol. 9(2), pp. 175–180.
Rosen et al. (1979) Exp. Neurology vol. 66, pp. 277–284.*
"Prolonged Pretreatment with alpha–Lipoic Acid Protects Cultured Neurons Against Hypoxic, Glutamate–, or Iron––induced Injury" Muller et al. J. Cereb. Blood Flow Metab. vol. 15, pp. 624–630 (1995).*
"Neuroprotective Activity of Lipoic Acid and Dihydrolipoic Acid" Wolz et al. Antiox. Health Dis. 6. pp. 205–225. (1997).*
Bauman et al., (2000) Journal Neurotrauma 17(8):679–693.
Beal, M. F., et al., Coenzyme $Q_{10}$ And Nicotinamide Block Striatal Lesions Produced By The Mitochondrial Toxin Malonate, (1994) Ann. Neurol. 36:882–888.
Desagher, S., et al., Pyruvate Protects Neurons Against Hydrogen Peroxide–Induced Toxicity, (1997) J. Neuroscience 17(23):9060–9067.
Gotz et al., Effect Of Lipoic Acid On Redox State Of Coenzyme Q In Mice Treated With 1–methyl–4–phenyl–1, 2,3,6–tetrahdorpyridine And Diethyldithiocarbamate, (1994) Eur. J. Pharmacology–Molec. Pharm. Section 266:291–300.
Klocker et al., Free Radical Scavenging And Inhibition Of Nitric Oxide Synthase Potentiates The Neurotrophic Effects Of Brain–Derived Neurotrophic Factor On Axotomized Retinal Ganglion Cells In Vivo, (1998) J. Neurosci. 18(3):1038–1046.
Koenig, M. L., et al., Thyrotropin–Releasing Hormone (TRH) Attenuates Glutamate–Stimulated Increases In Calcium In Primary Neuronal Cultures, (1996) Brain Res. 730:143–149.
Koening, M. L. et al., (1999) Neurosci. Abs., 25.
Long, J.B., et al., (1996) J. Neurotrauma 13:149–162.
Lowenstein et al., Selective Vulnerability Of Dentate Hilar Neurons Following Traumatic Brain Injury: A Potential Mechanistic Link Between Head Trauma And Disorders Of The Hippocampus, (1992) J. Neuroscience 12(12):4846–4853.
Marshall, S.B., et al., A Multicenter Trial On The Efficacy Of Using Tirilazad Mesylate In Cases Of Head Injury, (1998) J. Neurosurg. 89(4):519–525.
Matthews, et al., Coenzyme $Q_{10}$ With Multiple Vitamins Is Generally Ineffective In Treatment Of Mitochondrial Disease, (1993) Neurol. 43:884–890.

(List continued on next page.)

Primary Examiner—Mukund J. Shah
Assistant Examiner—Zachary C. Tucker
(74) Attorney, Agent, or Firm—Elizabeth Arwine

(57) ABSTRACT

Methods of preventing, treating, or both preventing and treating CNS injury, disease, neurotoxicity or memory deficit in a subject by the administration of at least one lipoic acid compound to the subject are disclosed. Examples of CNS injuries or disease include traumatic brain injury (TBI), posttraumatic epilepsy (PTE), stroke, cerebral ischemia, neurodegenerative diseases of the brain such as Parkinson's disease, Dementia Pugilistica, Huntington's disease and Alzheimer's disease, brain injuries secondary to seizures which are induced by radiation, exposure to ionizing or iron plasma, nerve agents, cyanide, toxic concentrations of oxygen, neurotoxicity due to CNS malaria or treatment with anti-malaria agents, and other CNS traumas. Examples of lipoic acid compounds include alpha-lipoic acid (ALA), dihydrolipoic acid (DHLA), 2-(N,N-dimethylamine) ethylamido lipoate-HCL (LA-plus), the oxidized or reduced R- or S-isomers thereof, the metabolites of alpha-lipoic acid such as 6,8-bisnorlipoic acid and tetranorlipoic acid and analogs thereof. Also disclosed are pharmaceutical compositions and kits comprising at least one lipoic acid compound.

34 Claims, 6 Drawing Sheets

OTHER PUBLICATIONS

McIntosh, T.K., et al., Neuropathological Sequelae Of Traumatic Brain Injury: Relationship To Neurochemical And Biomechanical Mechanisms, (1996) Laboratory Investigation 74(2):315–342.

Nishikawa et al., Long–term Coenzyme $Q_{10}$ Therapy For A Mitochondrial Encephalomyopathy With Cytochrome C Oxidase Deficiency: A $^{31}P$ NMR Study, (1989) Neurol. 39:399–403.

Paxinos and Watson, The Rat Brain In Stereotaxic Coordinates, Academic Press, New York (1986).

Racine, R. Modification Of Seizure Activity By Electrical Stimulation: II. Motor–Seizure (1972) Electroencephalogr. Clin. Neurophysiol. 32:281–294.

Salazar, A.M., et al., Epilepsy After Penetrating Head Injury. I. Clinical Correlates: A Report Of The Vietnam Head Injury Study, (1985) Neurology 35:1406–1414.

Tirosh et al., Neuroprotective Effects Of α–Lipoic Acid And Its Positively Charged Amide Analogue, (1999) Free Rad. Biol & Med. 26(11/12):1418–1425.

Wolz & Kriglstein, Neuroprotective Effects Of α–Lipoic Acid And Its Enantiomers Demonstrated In Rodent Models Of Focal Cerebral Ischemia, (1996) Neuropharmacology 35:369–375.

\* cited by examiner

METHOD OF TREATING, PREVENTING OR INHIBITING CENTRAL NERVOUS SYSTEM INJURIES AND DISEASES

RELATED APPLICATION DATA

This application claims the benefit of U.S. Provisional Patent Application No. 60/198,958, filed Apr. 21, 2000, naming James L. Meyerhoff, Debra L. Yourick and Michael L. Koenig as inventors, which is herein incorporated by reference.

ACKNOWLEDGEMENT OF GOVERNMENT INTEREST

This invention was made by employees of the United States Army. The government has rights in the invention.

BACKGROUND OF THE INVENTION

1. Field of the Invention

The invention relates to a method of treating, preventing or inhibiting central nervous system (CNS) injuries and diseases. In particular, the invention relates to a method of treating, preventing or inhibiting a CNS injury or disease in a subject by the administration of at least one lipoic acid compound to the subject.

2. Description of the Related Art

Traumatic brain injury (TBI) can initiate a cascade of events which may lead to dramatic elevation of intracranial pressure (ICP), cerebral edema, ischemia, intracranial hemorrhage and dysfunction of cerebrovascular regulatory mechanisms essential for survival. Deficits in memory, attention, and perception, emotional disorders, social behavioral problems, seizures (including non-convulsive seizures), paralysis, aphasia, post-traumatic epilepsy (PTE), and oxidative stress-induced neurotoxicity may result from TBI.

In several studies of severely head-injured patients, over 80% had ischemic damage in the hippocampus. See McIntosh, T. K., et al., (1996) Laboratory Investigation 74(2):315–342. The hippocampal damage may explain the prevalence of memory defects in survivors of TBI. Generally, the two main stages in the development of TBI are (1) primary, including contusion, laceration, intracranial hemorrhage and diffuse axonal injury; and (2) secondary, including delayed effects such as seizures, ischemia, edema, and biochemical reactions, which lead to necrosis and apoptosis.

Penetrating brain injuries, associated with retained intracranial ferric metal fragments and inevitably associated with hemorrhage, are highly likely to produce posttraumatic epilepsy (PTE). See Salazar, A. M., et al., (1985) Neurology 35:1406–1414. Development of seizures following penetrating craniocerebral trauma has been associated with the presence of hematoma, total brain volume loss, presence of retained metal fragments, hemiparesis, aphasia, visual field loss, organic mental disorder, headache and a history of seizures during the first year post injury.

Initial events in TBI such as hemorrhage and ischemia can elicit activation of leukocytes and excessive release of the excitatory neurotransmitter glutamic acid with resulting excess influx of calcium. These events can trigger a number of interactive intermediate reactions which can lead ultimately to neurotoxicity. These include decompartmentalization of iron, and the activation of several enzymes including phospholipases, xanthine oxidase, intraneuronal nitric oxide synthase and poly[ADP-ribose]polymerase (PARP). Formation of neurotoxic reactive oxygen species (ROS) appears to be a result common to many of these "initiator" pathways and is a major "perpetrator" in mediating necrotic neuronal death. For example, it is well-known that glutamate, acting via both NMDA and non-NMDA receptors, leads to increased intraneuronal calcium, which in turn may activate (a) phospholipase A2, triggering arachidonic acid production, or (b) xanthine oxidase. Both pathways lead to the production of free radicals, such as superoxide. Additional pathways leading to free radical formation include liberation of "catalytic" iron from extravasated hemoglobin and decompartmentalization of iron or copper from damaged mitochondria. Thus, although the immediate mechanisms of pathologic responses to nervous system may vary, many forms of neurotoxicity are believed to share a common final pathway via formation of ROS, reactive nitrogen species, or both.

ROS are most aggressively damaging in the central nervous system (CNS) as ROS attack double bonds in the unsaturated fatty acids, which are abundant in CNS membranes, to form carbon-centered radicals (R) or (R—HC—R) wherein "R" generally refers to any carbon chain which length may vary. These radicals initiate a chain reaction of lipid peroxidation, which continues until arrested by the formation of a relatively non-reactive species such as oxidized vitamin E or vitamin C. Scavengers, such as vitamin E, also known as alpha-tocopherol, donate a hydrogen atom to a radical, thereby becoming a secondary radical. Since the tocopherol radical is rather stable, it breaks the chain reaction, hence these scavengers are known as "chain-breaking antioxidants".

The several neurotoxic pathways can produce a variety of small, diffusible ROS, including superoxide, nitric oxide, peroxyl, perhydroxyl, peroxynitrite, hypochlorous and singlet oxygen. The antioxidant enzyme superoxide dismutase converts the superoxide radical to hydrogen peroxide, a non-radical oxidizing agent that can engage in a number of iron-catalyzed reactions producing the very toxic hydroxyl ion. For example, the ferrous ion can trigger the Fenton reaction with hydrogen peroxide to form hydroxyl ions plus a ferric ion. Iron ions can also catalyze the Haber-Weiss reaction, in which superoxide and hydrogen peroxide react to form hydroxyl ions and molecular oxygen. Superoxide can also react with nitric oxide to produce the intermediate peroxynitrite, which subsequently yields the hydroxyl radical.

Although a particular neurotoxic reaction might predominate initially, other pathways may rapidly be recruited, thereby exacerbating damage. For example, hemoglobin, a potential source of catalytic iron, potentiates excitatory amino acid-induced neurotoxic injury in cortical cell culture. Ischemia is a secondary effect of TBI and causes a metabolic imbalance wherein mitochondria increase production of ROS while decreasing production of energy required for neuronal homeostasis, engendering oxidative stress. Injury-induced activation of PARP can deplete NAD+, and consequently also deplete ATP. Depletion of energy sources such as ATP transforms glutamic acid from neurotransmitter to neurotoxin. Moreover, ROS exacerbate the excitotoxic pathways by increasing the release of glutamate and inhibiting its reuptake inactivation.

There are important endogenous antioxidant defenses in the central nervous system which are essential in providing cellular resilience in response to injury. These protective mechanisms include glutathione (GSH), alpha-lipoic acid (ALA), dihydrolipoic acid (DHLA), coenzyme Q, vitamin E, vitamin C, pyruvate, melatonin, and niacinamide. Some of these are synthesized endogenously and some are dietary requirements. The sulfhydryl group of GSH is particularly important in protecting cell membranes against peroxidative stress. GSH peroxidase, using GSH as a co-substrate and selenium as a metallic cofactor, reduces intracellular formation of hydrogen peroxide and free radicals.

Unfortunately, these endogenous antioxidant defenses in the central nervous system are not sufficient to prevent or inhibit TBI, PTE and other related CNS traumas. Consequently, various compounds and treatments have been developed.

Additionally, recent clinical trials of Tirilazad™ (Upjohn) and Peg-SOD (superoxide dimutase linked to polyethylene glycol) have been disappointing, their design has been controversial, and leaves the question of the value of antioxidants unresolved. See Marshall, S. B., et al., (1998) J. Neurosurg. 89(4):519–525. Tirilazad™ is an antioxidant aminosteroid which proved to be clinically unsuccessful against stroke because it did not readily cross the blood brain barrier and it failed to protect the hippocampus. Furthermore, a number of large clinical trials have failed to demonstrate a benefit of administering phenytoin, phenobarbital, carbamazepine or valproate as a way to prevent the onset of PTE.

Clearly, a need exists for effectively treating and preventing TBI, PTE and other CNS traumas.

SUMMARY OF THE INVENTION

In some embodiments, the present invention relates to a method of treating a subject suffering from a CNS injury or disease comprising administering to the subject a composition comprising a therapeutically effective amount of at least one lipoic acid compound.

In some embodiments, the present invention relates to a method of preventing or inhibiting a CNS injury or disease in a subject comprising administering to the subject a composition comprising a therapeutically effective amount of at least one lipoic acid compound.

In some embodiments, the invention relates to a method of preventing, inhibiting or treating neurotoxicity or memory deficit in a subject comprising administering to the subject a composition comprising a therapeutically effective amount of at least one lipoic acid compound.

Where the memory deficit may be induced by electroconvulsive shock therapy for treating diseases and disorders such as depression and schizophrenia, the composition may be administered before the electroconvulsive shock therapy to mitigate memory loss.

In some embodiments, the CNS injury or disease may be traumatic brain injury (TBI), posttraumatic epilepsy (PTE), stroke, cerebral ischemia, or a neurodegenerative disease. In some embodiments, CNS injury may be induced by fluid percussion, a blunt object impacting the head of the subject, an object which penetrates the head of the subject, or exposure to radiation, ionizing or iron plasma, a nerve agent, cyanide, toxic concentrations of oxygen, CNS malaria, or an anti-malaria agent.

In the embodiments of the invention, the lipoic acid compound may be alpha-lipoic acid (ALA), dihydrolipoic acid (DHLA or DHL), 2-(N,N-dimethylamine) ethylamido lipoate-HCL (LA-plus), the oxidized or reduced R- or S-isomers, a metabolite of α-lipoic acid, or an analog thereof. In preferred embodiments, the lipoic acid compound is ALA, DHLA, or LA-plus.

In some embodiments of the invention, the composition may further comprise at least one ROS scavenger. Suitable ROS scavengers include coenzyme Q, vitamin E, vitamin C, pyruvate, melatonin, niacinamide, N-acetylcysteine, GSH, and nitrones.

In the embodiments of the present invention, the therapeutically effective amount of the lipoic acid compound administered to the subject is about 0.001 mg to about 20 mg per kg of the subject, preferably about 1 mg to about 10 mg per kg of the subject, more preferably about 3 mg to about 10 mg per kg of the subject.

In some preferred embodiments, the total daily amount of the lipoic acid compound administered to the subject is about 50 mg to about 1200 mg, preferably about 100 mg to about 1000 mg, more preferably about 200 mg to about 800 mg, even more preferably about 300 mg to about 600 mg.

In some embodiments, the invention relates to administering the lipoic acid compound to a subject a period of time before the subject is exposed or likely to be exposed to a risk of CNS injury or damage or before the subject is exposed to conditions likely to cause neurotoxicity or memory deficit or both. The conditions likely to cause CNS injury or damage, neurotoxicity or memory deficit include electroconvulsive shock therapy, traumatic brain injury (TBI), posttraumatic epilepsy (PTE), stroke, cerebral ischemia, neurodegenerative diseases, fluid percussion, a blunt object impacting the head of the subject, an object penetrating the head of the subject, radiation, ionizing or iron plasma, nerve agents, cyanide, toxic concentrations of oxygen, CNS malaria, and anti-malaria agents. Other conditions likely to cause CNS injury or damage, neurotoxicity or memory deficit include certain medical procedures or conditions associated with risk for CNS ischemia, hypoxia or embolism such as brain tumor, brain surgery, open heart surgery, carotid endarterectomy, repair of aortic aneurysm, atrial fibrillation, cardiac arrest, cardiac or other catheterization, phlebitis, thrombosis, prolonged bed rest, prolonged stasis (such as during space travel or long trips via airplane, rail, car or other transportation), CNS injury secondary to air/gas embolism or decompression sickness.

The period of time may be about 72 hours to about the time of expected exposure, preferably about 48 hours to about the time of expected exposure, more preferably about 12 hours to about the time of expected exposure, even more preferably about 4 hours to about the time of expected exposure, and most preferably about 2 hours to about the time of expected exposure.

The administration of the lipoic acid compound may be continuous from the initial time of treatment to the end of treatment. For example, a transdermal patch or a slow-release formulation may be used to continually administer the lipoic acid compound to the subject for a given period of time. Alternatively, the lipoic acid compound may be administered to the subject periodically. For example, the lipoic acid compound may be first administered at about 24 hours before the time of expected exposure and then administered at about every 2 hours thereafter. In some embodiments, at least one ROS scavenger such as coenzyme Q, vitamin E, vitamin C, pyruvate, melatonin, niacinamide, N-acetylcysteine, GSH, or a nitrone, is administered prophylactically in combination with the prophylactic administration of the lipoic acid compound.

In the embodiments of the invention, the composition may further comprise a pharmaceutically acceptable excipient. The composition may be administered intravenously, intradermally, subcutaneously, orally, transdermally, transmucosally or rectally. Preferably, the composition is orally administered.

In some embodiments, the invention relates to a pharmaceutical composition for treating or preventing CNS injury, disease or neurotoxicity in a subject comprising a therapeutically effective amount of at least one lipoic acid compound and a pharmaceutically acceptable excipient. The lipoic acid compound may be ALA, DHLA, LA-plus, the oxidized or reduced R- or S-isomers, a metabolite of ALA, or an analog thereof. The pharmaceutical composition may further comprise at least one ROS scavenger. Examples of suitable ROS ts scavengers include coenzyme Q, vitamin E, vitamin C, pyruvate, melatonin, niacinamide, N-acetylcysteine, GSH, and nitrones.

In some embodiments, the invention relates to a kit comprising a composition comprising a therapeutically effective amount of at least one lipoic acid compound. The lipoic acid compound may be ALA, DHLA, LA-plus, the oxidized or reduced R- or S-isomers, a metabolite of ALA, or an analog thereof. In a preferred embodiment, the lipoic acid compound is ALA, DHLA, or LA-plus. The kit or the composition may further comprise at least one ROS scavenger. Suitable ROS scavengers include coenzyme Q, vitamin E, vitamin C, pyruvate, melatonin, niacinamide, N-acetylcysteine, GSH, and nitrones. The kit may further comprise a device for administering the composition to a subject such as an injection needle, an inhaler, a transdermal patch. The kit may also comprise instructions for use.

DESCRIPTION OF THE DRAWINGS

This invention is further understood by reference to the drawings wherein.

DETAILED DESCRIPTION OF THE INVENTION

The present invention relates to a method of preventing, treating, or both preventing and treating a CNS injury or disease by the administration of at least one lipoic acid compound.

Examples of CNS injuries or disease include TBI, stroke, concussion (including post-concussion syndrome), cerebral ischemia, neurodegenerative diseases of the brain such as Parkinson's disease, Dementia Pugilistica, Huntington's disease and Alzheimer's disease, brain injuries secondary to seizures which are induced by radiation, exposure to ionizing or iron plasma, nerve agents, cyanide, toxic concentrations of oxygen, neurotoxicity due to CNS malaria or treatment with anti-malaria agents, and other CNS traumas. Examples of lipoic acid compounds include alpha-lipoic acid (ALA), dihydrolipoic acid (DHLA or DHL), 2-(N,N-dimethylamine) ethylamido lipoate-HCL (LA-plus), the oxidized or reduced R- or S-isomers, the metabolites of ALA such as 6,8-bisnorlipoic acid and tetranorlipoic acid and analogs thereof. Analogs of lipoic acid compounds include lipoamides.

ALA is a physiological constituent of mitochondrial membranes and is an essential cofactor in the oxidative decarboxylation of alpha-keto acids such as pyruvate and alpha-ketoglutarate. ALA is present in food and in mammalian tissues. ALA is clinically safe, well-tolerated and is currently used to treat peripheral neuropathy in patients with diabetes. ALA is stable in tablet form, can be given orally, has good bioavailability in humans, is well-tolerated and is endogenously converted to DHLA.

Both ALA and DHLA are effective scavengers of numerous ROS and have been shown to be neuroprotective in several rodent models of cerebral ischemia. They are rapidly distributed to the central nervous system, improve memory, are active in both lipid and aqueous phases, and increase intracellular levels of GSH and ATP.

ALA and DHLA may be used in methods for treating or prevention TBI, PTE and to other CNS traumas. In particular, they protect neurons, among other things, by (1) acting as direct chain-breaking antioxidants; (2) recycling the antioxidant vitamins C and E; (3) scavenging at least 8 types of free radicals; (4) chelating decompartmentalized iron ions; (5) chelating copper ions; (6) increasing intracellular energy stores which include ATP; (7) regenerating and increasing intracellular levels of the endogenous antioxidant, glutathione; (8) increasing the ratio of reduced to oxidized coenzyme Q; and (9) providing methionine sulfoxide reductase with reducing equivalents. DHLA also enhances the repair of oxidatively damaged proteins.

Figure 1:
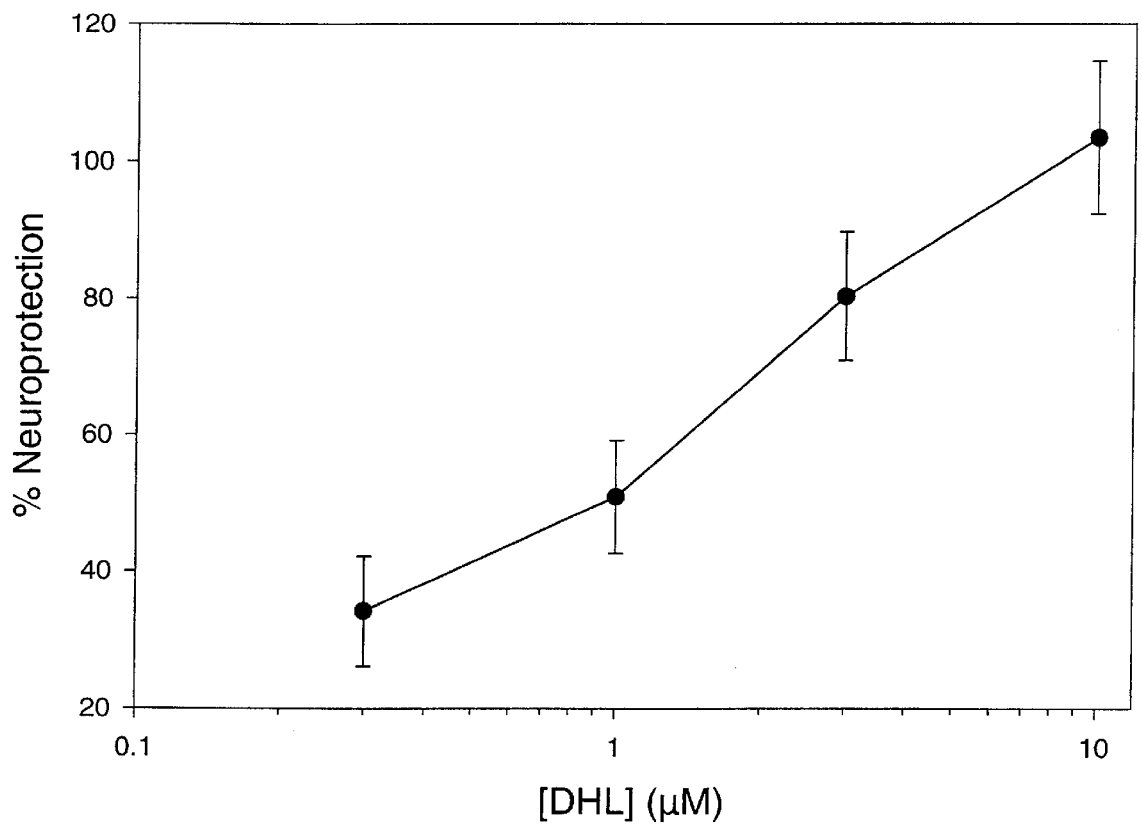
FIG. 1 illustrates that DHLA is protective in a concentration-related manner against hemoglobin-induced toxicity in cultured neurons in Vitro.

As illustrated in FIG. 1, DHLA was recently demonstrated to be protective in a concentration-related manner (about 0.3 to about 10 micromolar) against hemoglobin-induced toxicity in cultured neurons in vitro. See Koenig et al., (1999) Neurosci. Abs., 25, which is herein incorporated by reference. Here, primary cultures of neurons derived from the forebrains of E-15 rat fetuses were pre-incubated with DHLA at several different concentrations for about 4 hours. The neurons were then exposed to about 10 micromoles of hemoglobin and resulted in about 50% viability after about a 24 hour exposure. Neuronal viability was assessed by using the calorimetric MT assay of succinate dehydrogenase activity. MTT is a calorimetric dye, 3-(4,5-dimethylthiazol-2-yl)-2,5-diphenyltetrazolium bromide, and is available from Sigma. Neuroprotection increased with increasing concentrations of DHLA. There was no evidence of neuroprotection where DHLA was co-applied with hemoglobin.

Figure 2:
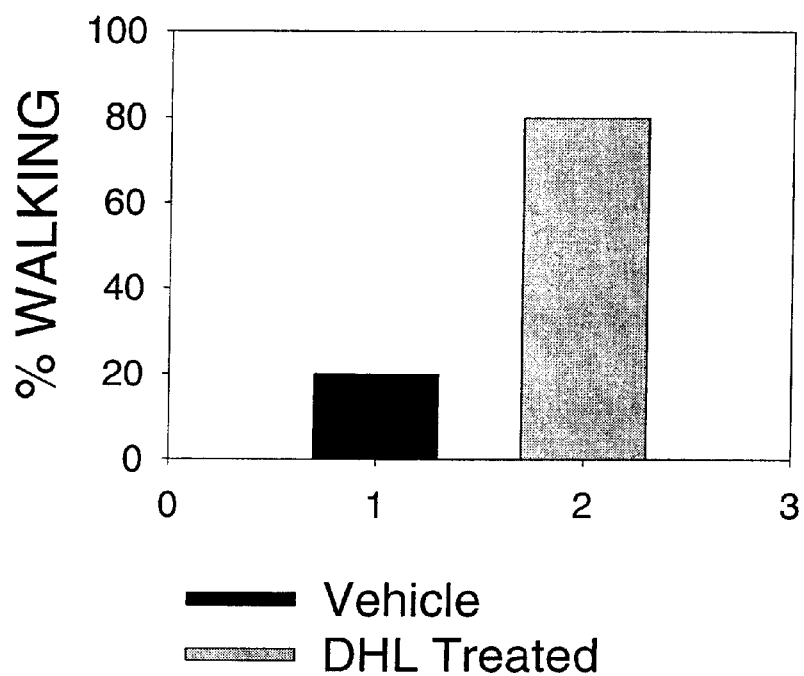
FIG. 2 illustrates that DHLA is protective against experimental spinal cord injury in rats in vivo.

As illustrated in FIG. 2, DHLA was also demonstrated to be protective against experimental spinal cord injury in rats in vivo. Here, about 5 micromoles of DHLA was administered intrathecally as a 2 hour pretreatment. Flaccid paralysis was acutely evident about 10 minutes after injection with dynorphin A and where there was no pretreatment with DHLA or co-treatment with DHLA. Pretreatment with DHLA and treatment after injury with DHLA was observed to improve motor scores. See Long et al., (1999) Neurosci. Abs. 25, which is herein incorporated reference.

Figure 3A:
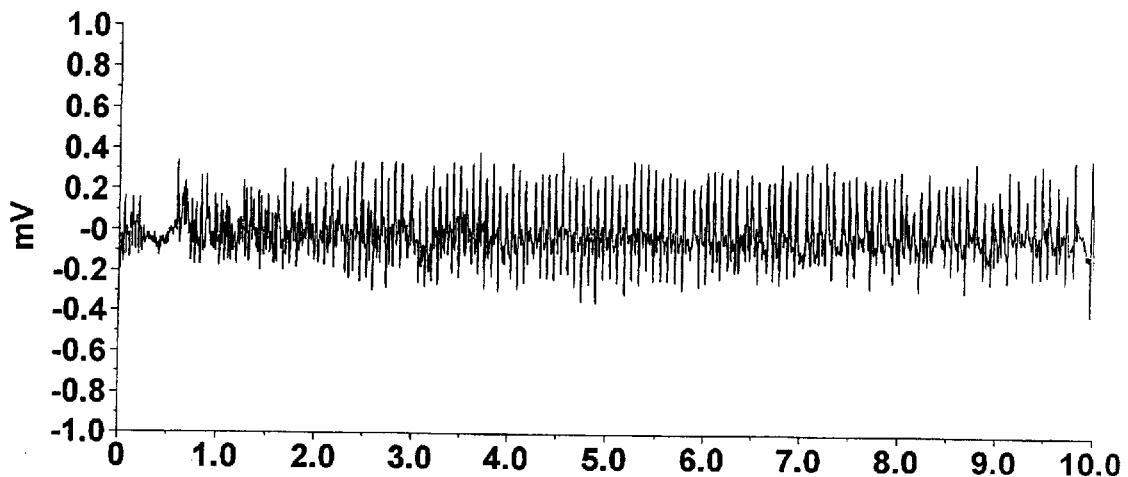
FIG. 3a is an example of an iron-induced paroxysmal spiking seizure on electroencephalogram (EEG) in rat.
Figure 3B:
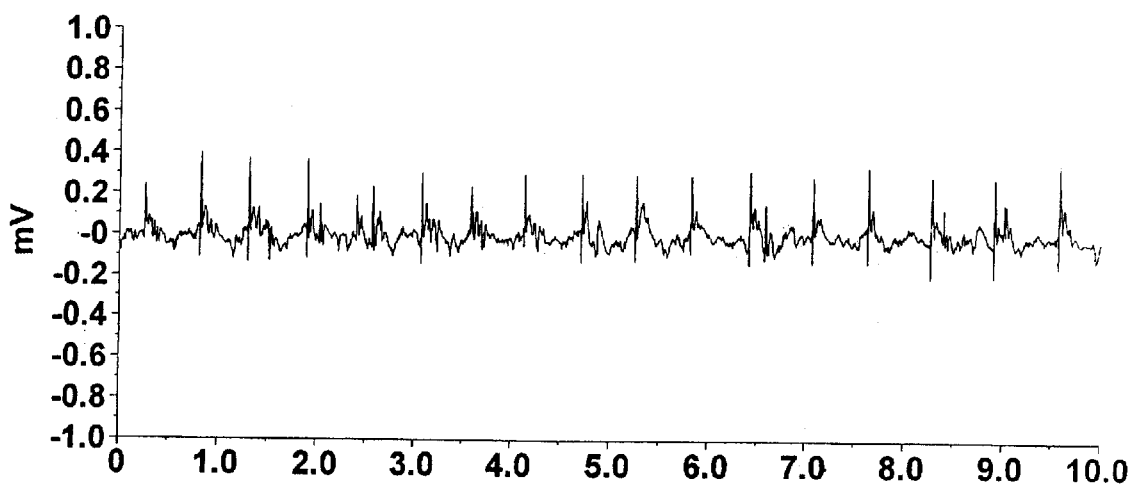
FIG. 3b is an example of an iron-induced spike-and-wave seizure on electroencephalogram (EEG) in rat.
Figure 4:
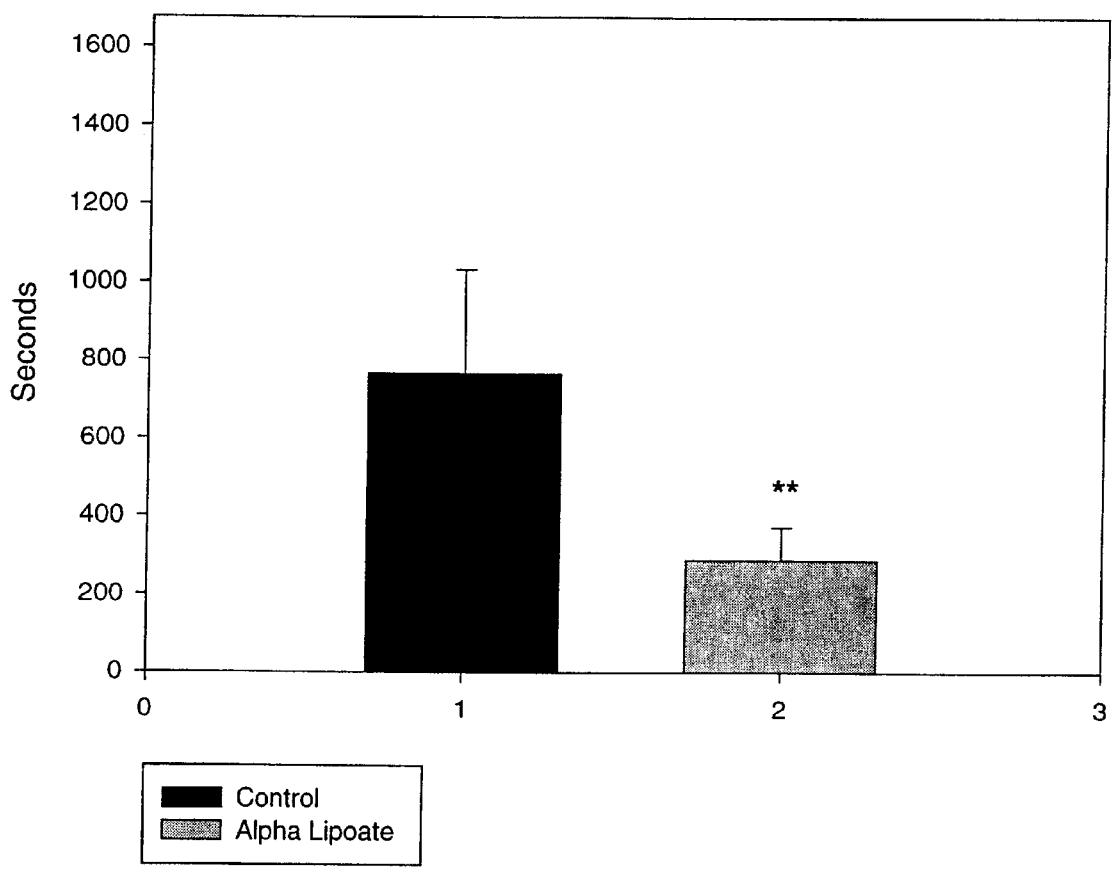
FIG. 4 illustrates that pretreatment with ALA and co-treatment with DHLA reduces iron chloride-induced seizure activity by about 55%.

A modified Willmore model of ferric chloride-induced epilepsy may be used to automatically record and quantify seizure activity on a 24 hour basis as shown in FIGS. 3a and 3b. Here, ferric chloride was injected into the cerebral cortex of a rat which elicits intense seizures. FIG. 3a shows an example of an electroencephalograph (EEG) paroxysmal spiking seizure pattern. FIG. 3b shows an example of an EEG "spike and wave" seizure pattern. By using this modified neurotoxic model, as illustrated in FIG. 4, pretreatment with α-LA and co-treatment with DHLA reduced iron chloride-induced seizure activity by about 55%. In this experiment, male Sprague Dawley rats were injected with 100 mg/kg of ALA i.p. once daily for 48 hours then anesthetized and 50 mg/kg of DHLA was injected i.p. after which 600 micromolar of ferric chloride was injected unilaterally intracortically. EEG was recorded for 24 hours and sampled for 10 seconds for each 60 seconds over a period of 24 hours. To achieve uniformly quantitative information, the number of seconds of seizure activity was measured in every sampled 10 seconds. As shown in FIG. 4, rats pretreated with alpha-LA and DHLA had about 55% less seizure activity than rats that were not pretreated.

LA-plus is a positively charged water soluble lipoic acid amide analog which shows a higher rate of intracellular reduction and retention than is seen with ALA, as well as better in vitro protection against glutamate-induced loss of GSH, formation of peroxide and neurotoxicity in cultured mouse hippocampal HT4 cells. See Tirosh et al., (1999) Free Rad. Biol & Med. 26(11/12):1418–1426, which is herein incorporated by reference.

In addition to the administration of a lipoic acid compound, at least one ROS scavenger may also be administered. Examples of ROS scavengers include coenzyme Q, vitamin E, vitamin C, pyruvate, melatonin, niacinamide, N-acetylcysteine, GSH and nitrones.

The neuroprotective efficacy of the lipoates may be enhanced by supplementary compounds. For example, the neuroprotective efficacy of the lipoates might be enhanced by (1) combination with other free radical scavenger with slightly differing mechanisms of action (e.g. coenzyme Q; or nitrones); or (2) with other classes of neuroprotectants with fundamentally different mechanisms, such as the neurotrophic factors brain-derived neurotrophic factor (BDNF), nerve growth factor (NGF), neurotrophins (e.g. NT-3) and/or the neuroprotective endogenous TRH analog, pyroGlu-Glu-Pro (known by its abbreviation, EEP).

Coenzyme Q10 (CoQ10), also known as ubiquinone, is an endogenous molecule that transports electrons in mitochondria, as part of the process of ATP generation. CoQ10 levels in spinal cord have been reported to be decreased following injury and the changes were found to be reflective of the degree of trauma. Ubiquinone 10 has been found to be a lipid-soluble antioxidant which can prevent lipid peroxidation in brain synaptosomes and mitochondria, recycle vitamin E and scavenge ROS. Pretreatment with coenzyme Q reduced malonate-induced neurotoxicity in vivo. See Beal et al., (1994) Eur. J. Pharmacology—Molec. Pharm. Section 266:291–300, which is herein incorporated by reference. Although some studies reported that it was therapeutically efficacious in certain clinical situations, others have found it ineffective. See Nishikawa et al., (1989) Neurol. 39:399–403; Matthews, et al., (1993) Neurol. 43:884–890, which are herein incorporated by reference. However, it is clearly an antioxidant neuroprotectant which may be synergistic with alpha-LA much as it synergizes with niacinamide. See Gotz et al., (1994) Eur. J. Pharmacology—Molec. Pharm. Section 266:291–300; Beal, et al., (1994) Ann. Neurol. 36:882–888, which are herein incorporated by reference. Accordingly, coenzyme Q may be co-administered with the lipoic acids of the invention.

Nitrone-based free radical traps (nitrones) such as alpha-Phenyl-N-tert-butylnitrone (PBN), N-tert-Butyl-α-(2-sulfophenyl)nitrone (SPBN), Azulenyl nitrones, and NXY-059, offer a ROS scavenging mechanism which differs from vitamin E, the lipoic acids and other endogenous compounds. The nitrones react covalently with ROS to form stable nitroxides. They have also been shown to be neuroprotective against glutamate-induced toxicity in cultured neurons as well as in several rodent models of cerebral ischemia, including transient global ischemia, transient and permanent occlusion of the middle cerebral artery. Therefore, nitrones may be co-administered with the lipoic acids of the invention.

SPBN is an effective neuroprotectant without significant toxicity. The free radical scavenger SPBN is synergistic with brain-derived neurotrophic factor (BDNF) in survival of axotomized retinal ganglion cells. See Klocker et al., (1998) J. Neurosci. 18(3):1038–1046, which are herein incorporated by reference. Thus, BDNF may be co-administered with the lipoic acids of the invention. PBN is a nitrone which has been shown to be neuroprotective in animal models of ischemia, even when administered post injury. PBN is also effective as a pre-treatment against DFP-induced convulsions.

Figure 5:
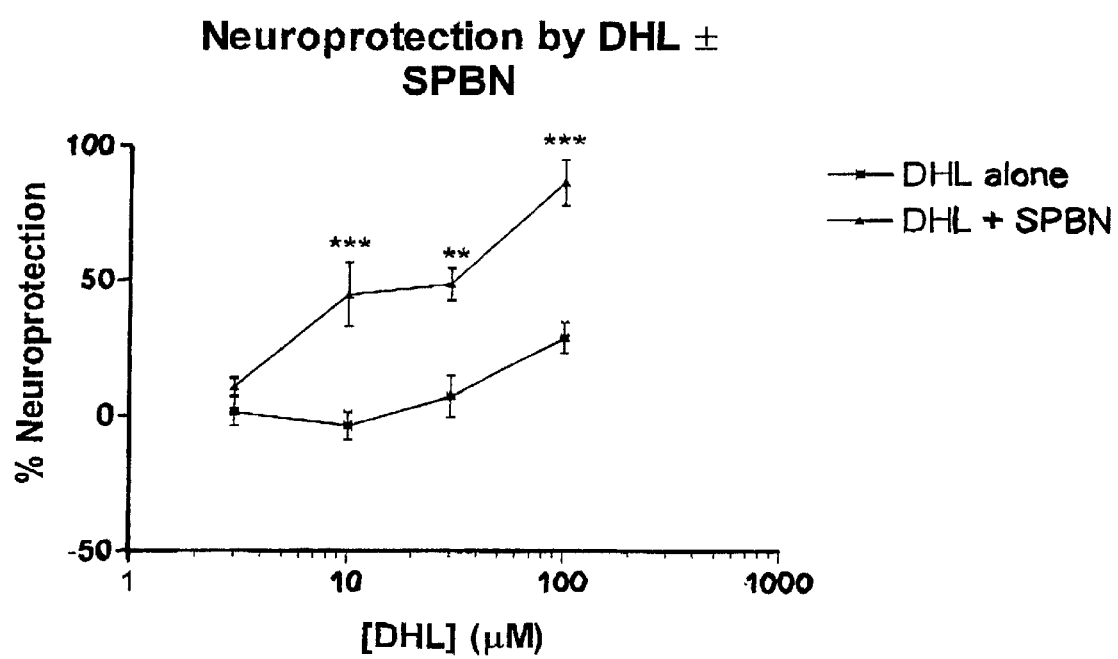
FIG. 5 illustrates the neuroprotective effects of DHL and SPBN.
Figure 6:
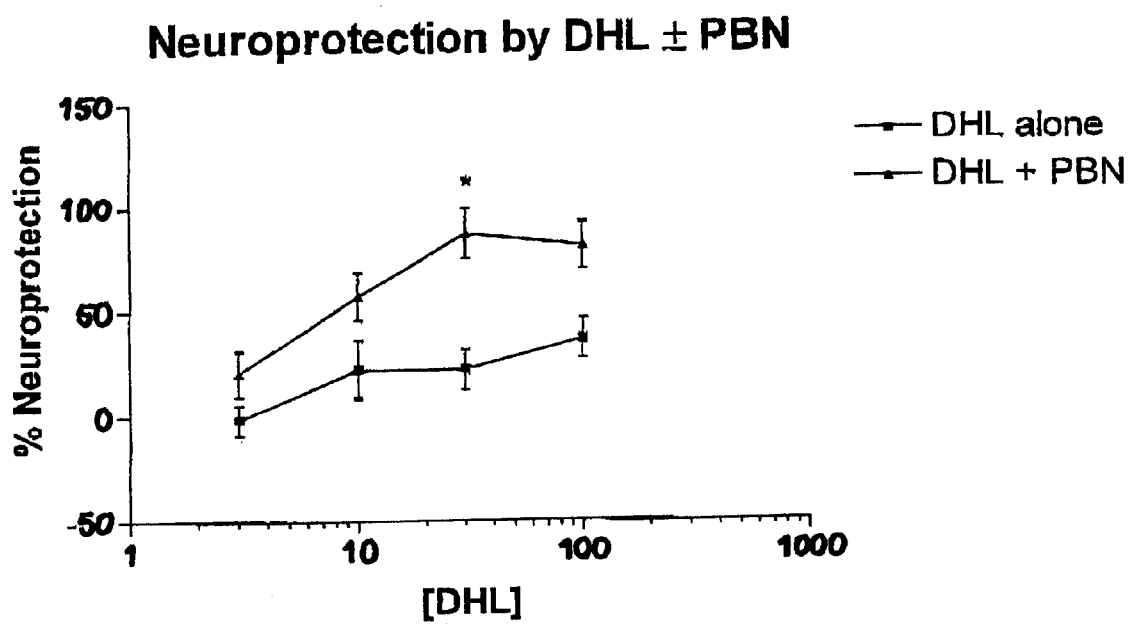
FIG. 6 illustrates the neuroprotective effects of DHL and PBN.

As described in Example 7 and shown in FIGS. 5 and 6, since nitrones have more than one mode of action, as do the lipoic acids, and since the scavenging mechanisms of nitrones and lipoic acids differ, nitrones may be co-administered with lipoic acids to provide a synergistic neuroprotective effect.

Since one group of compounds such as lipoic acids might be more suitable for pretreatment, and another group such as nitrones might be more suitable for post-injury treatment, the times and amounts that the lipoic acid compounds and the supplementary compounds are administered may be varied. For example, an individual known to be at risk for certain injuries may be administered a, lipoate. After an injury occurs, the individual would be administered a supplementary active compound such as a nitrone, trophin, or other free radical scavenger. The lipoate administered before the injury would confer a protection at the time of injury and afterwards. The post-injury administration of the supplementary active compound would provide a synergistic neuroprotective effect with the lipoate.

A tripeptide comprising three linked amino acids, pyroglutamate-glutamate-proline-amide, which is referred to as EEP, is structurally similar to thyrotropin releasing hormone (TRH) which comprises pyroglutamate-histidine-proline. Both EEP and TRH are found in the brain. Like TRH, EEP is neuroprotective against Glutamate-induced neurotroxicity. But unlike TRH, EEP is not hydrolyzed in plasma by the TRH-hydrolyzing enzyme thyroliberinase. Thus, EEP has better clinical neuroprotective potential than TRH. However, either EEP or TRH or both may be administered in combination with the lipoic acids of the invention.

Vitamin E, alpha-Tocopherol, is a normal dietary component and prevents peroxidative injury of sulfhydryl groups of glycolipids and glycoproteins by augmenting the antioxidant effects of enzyme systems such as glutathione peroxidase. It stimulates the synthesis of ATP, decreases lipid peroxidation, attenuates neurotoxic effects of iron in vitro. and prevents iron-induced seizures in vivo. Although vitamin E exhibits a slow rate of absorption through the blood brain barrier and is not suitable in methods to rapidly treat a brain injury, vitamin E may be suitable for prophylactic treatments and treatments over long periods of time.

As ischemia induces a significant decrease of the activity of E1 component of the pyruvate dehydrogenase complex and DHLA protects the E1 component from chemical inactivation, the lipoic acid compounds of the present invention may be coupled via an amide linkage to one of the three enzymes of the pyruvate dehydrogenase complex.

In the method of the present invention, a therapeutically effective amount of at least one lipoic acid compound or an analog thereof may be given prophylactically to a subject having a high risk for obtaining a CNS injury or disease. A subject pretreated with a lipoic acid compound or analog thereof would have an increased antioxidant reserve and would therefore have an increased resistance to CNS injuries and diseases. Administration of the lipoic acid compound may be continued after obtaining the CNS injury or disease.

Lipoic acid compounds may be administered to a subject as a method of preventing or treating CNS damage induced by exposure to nerve agents such as Soman, sarin, VX and the like. Soman elicits a sustained increase in extracellular glutamate levels in the amygdala, induces the de-compartmentalization of iron in brain tissue and catalyzes the formation of ROS.

Lipoic acid compounds may be administered to a subject as a method of preventing or treating radiation-induced CNS damage as inhibition of free radical formation provides neuroprotection to cultured cortical neurons exposed to ionizing radiation and injections of lipoic acid protects hematopoietic tissues in gamma-irradiated mice. Lipoic acid should also protect against injury to CNS, cardiac and hematopoeitic tissues secondary to cancer chemotherapy.

Additionally, lipoic acid compounds may be administered to a subject suffering from CNS malaria or a subject being treated with Arteether and related antimalarial compounds as a method to prevent or treat CNS damage.

Further, the lipoic acid compounds may be administered to a subject exposed to high oxygen under pressure (OHP) as the pathophysiological mechanism in toxicity induced by OHP may involve free radical generation. OHP causes seizures and convulsions.

The lipoic acid compounds may be administered prophylactically to a subject at risk for CNS injury or disease. Subjects at risk for CNS injury or disease include participants in contact sports such as football and boxing, military personnel, astronauts and others at risk for exposure to blast overpressure, blunt head trauma, and penetrating brain injury. The lipoic acid compounds may be administered intravenously, intradermally, subcutaneously, orally, transdermally, transmucosally or rectally.

A therapeutically effective amount of the lipoic acid compound of the invention may be administered to a subject a period of time before the subject is exposed to a risk of CNS injury or damage or before the subject is exposed or likely to be exposed to conditions likely to cause neurotoxicity or memory deficit or both. The conditions likely to cause CNS injury or damage, neurotoxicity or memory deficit include electroconvulsive shock therapy, traumatic brain injury (TBI), posttraumatic epilepsy (PTE), stroke, cerebral ischemia, neurodegenerative diseases, fluid percussion, a blunt object impacting the head of the subject, an object penetrating the head of the subject, radiation, ionizing or iron plasma, nerve agents, cyanide, toxic concentrations of oxygen, CNS malaria, and anti-malaria agents. The period of time may be about 72 hours to about the time of expected exposure, preferably about 48 hours to about the time of expected exposure, more preferably about 12 hours to about the time of expected exposure, even more preferably about 4 hours to about the time of expected exposure, and most preferably about 2 hours to about the time of expected exposure. It is to be understood, however, that the lipoic acid compound may be administered at a period of time which is more than about 72 hours before the time of expected exposure. For example, the period of time may be about 7 days before the expected exposure. The administration of the lipoic acid compound may be continuous from the initial time of treatment to the end of treatment. For example, a transdermal patch or a slow-release formulation may be used to continually administer the lipoic acid compound to the subject for a given period of time. Alternatively, the lipoic acid compound may be administered to the subject periodically. For example, the lipoic acid compound may be first administered at about 24 hours before the time of expected exposure and then administered at about every 2 hours thereafter.

ROS scavengers such as coenzyme Q, vitamin E, vitamin C, pyruvate, melatonin, niacinamide, N-acetylcysteine, GSH, and nitrones may also be administered prophylactically along with the lipoic acid compound. For example, as described in Beal, M. F., et al., (1994) Ann. Neurol. 36:882–888, which is herein incorporated by reference, therapeutically effective doses of coenzyme Q may be administered in combination with therapeutically effective doses of a lipoic acid compound. Additionally, neurotrophic factors such as brain-derived neurotrophic factor (BDNF), nerve growth factor (NGF), neurotrophins, and analogs thereof, may be administered prophylactically along with the lipoic acid compound.

The therapeutically effective amount of the lipoic acid compound administered prophylactically to the subject may be about 0.001 mg to about 20 mg per kg of the subject, preferably about 1 mg to about 10 mg per kg of the subject, more preferably about 3 mg to about 10 mg per kg of the subject. The total daily amount of the lipoic acid compound administered prophylactically to the subject may be about 50 mg to about 1200 mg, preferably about 100 mg to about 1000 mg, more preferably about 200 mg to about 800 mg, even more preferably about 300 mg to about 600 mg.

The lipoic acid compounds of the invention may be incorporated into pharmaceutical compositions suitable for administration. Such compositions typically comprise at least one lipoic acid or at least one analog thereof and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds such as ROS scavengers may also be incorporated into the compositions. Other supplementary active compounds include neurotrophic factors such as brain-derived neurotrophic factor (BDNF), nerve growth factor (NGF), neurotrophins, and analogs thereof.

A pharmaceutical composition of the invention is formulated to be compatible with its intended route of administration. Examples of routes of administration include parenteral, e.g., intravenous, intradermal, subcutaneous, oral, transdermal, transmucosal, and rectal administration. Solutions or suspensions used for parenteral, intradermal, or subcutaneous application may include a sterile diluent such as water for injection, a saline solution, a fixed oil, a polyethylene glycol, glycerine, propylene glycol or other synthetic solvent, an antibacterial agent such as benzyl alcohol or methyl paraben, an antioxidant such as ascorbic acid or sodium bisulfite, a chelating agent such as ethylenediaminetetraacetic acid, a buffer such as an acetate, citrate or phosphate and an agent for the adjustment of tonicity such as sodium chloride or dextrose. pH may be adjusted with acids or bases, such as hydrochloric acid or sodium hydroxide. Parenteral preparations may be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier may be a solvent or dispersion medium containing water, ethanol, a polyol such as glycerol, propylene glycol, and liquid polyetheylene glycol, and the like, and suitable mixtures thereof. The proper fluidity may be maintained by the use of a coating such as lecithin, by the maintenance of the required particle size in the case of dispersion or by the use of surfactants. Prevention of the action of microorganisms may be achieved by various antibacterial and antifungal agents such as parabens, chlorobutanol, phenol, ascorbic acid, thimerosal, and the like. In many cases, isotonic agents such as sugars, polyalcohols such as manitol, sorbitol, sodium chloride may be used in the composition. Prolonged absorption of the injectable compositions may be brought about by including an agent which delays absorption such as aluminum monostearate and gelatin.

Sterile injectable solutions may be prepared by incorporating the lipoic acid compound in the required amount in an appropriate solvent with one or a combination of ingredients enumerated above, as required, followed by filtered sterilization. Generally, dispersions are prepared by incorporating the lipoic acid compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the lipoic acid compound may be incorporated with excipients and used in the form of tablets, troches, or capsules. Pharmaceutically compatible binding agents, adjuvants, or both may be included as part of the composition. The tablets, pills, capsules, troches and the like may contain a binder such as microcrystalline cellulose, gum tragacanth or gelatin, an excipient such as starch or lactose, a disintegrating agent such as alginic acid, Primogel, or corn starch, a lubricant such as magnesium stearate or Sterotes, a glidant such as colloidal silicon dioxide, a sweetening agent such as sucrose or saccharin, or a flavoring agent such as peppermint, methyl salicylate, or orange flavoring.

For administration by inhalation, the compounds may be delivered in the form of an aerosol spray from pressured container or dispenser which contains a suitable propellant, e.g., a gas such as carbon dioxide, or a nebulizer.

Systemic administration may also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds may be prepared with carriers which protect the lipoic acid compounds against rapid elimination from the body, such as a controlled release formulation, implants and microencapsulated delivery systems. Biodegradable, biocompatible polymers such as ethylene vinyl acetate, polyanhydrides, polyglycolic acid, collagen, polyorthoesters, and polylactic acid may be used. Methods of preparing these formulations will be apparent to those skilled in the art. The materials may also be obtained commercially from Alza Corporation and Nova Pharmaceuticals, Inc. Liposomal suspensions can also be used as pharmaceutically acceptable carriers. These can be prepared according to methods known to those skilled in the art.

The pharmaceutical compositions may be formulated in dosage unit forms for ease of administration and uniformity of dosage. A dosage unit form, as used herein, refers to a physically discrete unit suitable for use as a unitary dosage for the subject to be treated. Each unit may contain a predetermined quantity of the lipoic acid compound calculated to produce the desired therapeutic effect in association with the required pharmaceutical carrier. The specification for the dosage unit form of the invention is dictated by and directly dependent on the unique characteristics of the particular lipoic acid compound and the particular therapeutic effect to be achieved.

Toxicity and therapeutic efficacy of the particular lipoic acid compound may be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Lipoic acid compound which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies may be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of the lipoic acid compound of the present invention (i.e., an effective dosage) ranges from about 0.001 mg to about 200 mg per kg of the subject, preferably about 25 mg to about 125 mg per kg of the subject, more preferably about 50 mg to about 100 mg per kg of the subject. Where the subject is human, the therapeutically effective amount ranges from about 0.001 mg to about 20 mg per kg of the human, preferably about 1 mg to about 10 mg per kg of the human, more preferably about 3 mg to about 10 mg per kg of the human.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a lipoic acid compound can include a single treatment or a series of treatments. Administration of the lipoic acid compound may be administered prophylactically before CNS trauma, in individuals at risk. The lipoic acid compound may be administered during and after CNS trauma. It is appreciated that the effective dosage of the lipoic acid compound may increase or decrease over the course of a particular treatment.

The following examples are intended to illustrate but not to limit the invention.

EXAMPLE 1

Cultured Cerebral Rat Neurons

Primary cultures may be established following the procedures outlined by Koenig, M. L., et al., (1996) Brain Res. 730:143–149, which is herein incorporated by reference. The forebrains of fetal rat pups (embryonic day 15) are isolated and the cells are dispersed by repeated trituration in neuronal culture medium (NCM). NCM comprises a 1:1 ratio of Ham's F-12 (Biofluids, Rockville, Md.) to Basal Medium Eagle (Sigma, St. Louis, Mo.), supplemented with 0.6 g/L of dextrose, 0.35% glutamine and 1% Pen-Strep (Biofluids. Rockville, Md.). Following centrifugation at 900×g for 5 minutes, the cells are plated onto poly-L-lysine-coated 48 well plates at a density of $10^6$ cells/ml. To suppress glial growth. the cultures are treated with cytosine arabinoside ($10^{-5}$ M) for 4 days. All cultures are maintained in an incubator comprising 5% $CO_2$ at 37° C. for about 6 days to about 15 days prior to use.

The cultured rat forebrain neurons are subjected to oxidative stress using hydrogen peroxide following the well-characterized paradigm by Desagher, S., et al., (1997) J. Neuroscience 17(23):9060–9067, which is herein incorporated by reference.

Oxidative injury is assessed by using an MTT assay (Sigma, St. Louis, Mo.). About 24 h after exposure to either hemoglobin or an oxidative insult, MTT is added to each test well such that the final concentration of the dye is about 0.15 mg/ml. Plates are returned to the incubator for about 1 hr at which time unincorporated MTU is removed and the plates are allowed to air dry. The purple formazan product indicative of viable cells is then dissolved by adding about 250 μl of acidified isopropanol comprising about 95% isopropanol and about 5% 2N HCl. About 200 μl aliquots are collected and the absorbance of these aliquots are measured on an ELISA plate reader at about 540 nm. Control (untreated) wells are included in each experiment, and viability is calculated as the percentage of mean control values for each plate.

The concentrations of ALA and LA-plus are about 25, about 50 and about 100 micromolar. The concentrations of selenium are about 10 and about 20 micromolar. The concentrations of pyruvate are about 0.3, about 1.0, and about 3.0 mM. The concentrations of SPBN ranges from about 1 to about 50 mM.

These studies are evaluated by multi-way analysis of variance. When a significant F score is found, an a posteriori or a priori test involving a multiple comparison of means, whichever is appropriate, is used to compare individual treatment groups.

EXAMPLE 2

Fluid Percussion

Male Sprague-Dawley rats weighing about 250 g to about 350 g, pretrained in neurobehavioral tasks described below, are surgically prepared for fluid percussion (FP) injuries using standard surgical procedures known in the art. See Long, J. B., et al., (1996) J. Neurotrauma 13:149–162, which is herein incorporated by reference. Surgical instruments and materials are steam-sterilized using an autoclave and are resterilized between repetitive surgeries using heated glass beads such as Steri 350, which are available from Inotech Biosystems Inc. (Lansing, Mich.).

Briefly, about 24 hr prior to the experiment, rats are anesthetized with about 70 mg/kg of ketamine and about 6 mg/kg xylazine administered i.m. and the scalp is shaved. The anesthetized rat is then placed in a stereotaxic apparatus and a surgical scrub of the scalp is performed. Using a one cc syringe and a 27 ga needle, the scalp is infiltrated with about 0.2 ml of a 1% lidocaine solution, a midline incision is made, and the scalp and temporal muscles are reflected.

Using a 4.8 mm diameter trephine, a craniotomy centered over the right parietal cortex is performed, leaving the dura intact. A stainless steel screw is inserted into the skull about 1 mm rostral to bregma. A plastic luer adapter (2.6 mm I.D., about 4.8 mm O.D.) is snugly seated into the craniotomy over the exposed dura, secured to the skull with cyanoacrylate adhesive, and embedded in dental acrylic. The connector is packed with sterile cotton and the surgical site is treated with bacitracin and lidocaine ointments. Rats are observed post-operatively and kept warm with a Vetko (Stoelting, Wood Dale, Ill.) thermal barrier until recovery from anesthesia (i.e. ambulatory), at which time they are returned to their home cages.

After being retested in the visual discrimination task to ensure a return to presurgery levels of accuracy the rats are anesthetized with halothane and prepared with femoral vein and tail artery catheters in experiments employing secondary hypoxia. Under aseptic conditions, the vessels are exposed by blunt dissection and PE 50 catheters filled with a sterile heparinized saline, about 10 USP units/ml, are inserted and secured using 3-O nylon sutures. Patency of the i.v. cannulae is maintained with about 0.2 ml flushes with heparinized saline immediately following drug or vehicle injections. The halothane anesthesia is maintained using compressed air and a continuous flow anesthesia system available from Stoelting (Wood Dale, Ill.) in combination with a Fluovac (Stoelting, Wood Dale, Ill.) halothane scavenger, which recaptures anesthetic gases by vacuum and thereby minimizes the escape of halothane to the ambient air.

The spontaneously breathing, anesthetized rats are then positioned in a stereotaxic apparatus, and the luer cranial connector is exposed, filled with sterile saline, and attached to a fluid percussion device. available from Dragonfly (Ridgeley, W.Va.). Briefly, with this device a fluid pressure pulse is generated in a 1 1/16 in. bore stainless steel cylinder with a 3 in. piston stroke that is filled with sterile water and connected to the cranial luer adapters using flexible high pressure tubing (0.089 in. i.d.). The injury is induced by striking the opposing piston with a weighted metal pendulum released from a predetermined height. The resultant rapid injection of a small volume of saline into the closed cranial cavity causes a pulse of increased intracranial pressure that is associated with a brief deformation of brain tissue. The pressure pulse is measured extracranially by a pressure transducer, Model 211B4, available from Kistler Instruments Corp. (Amherst, N.Y.) and recorded on a digital storage oscilloscope, Tecktronix 2212, (Tektronix Beaverton, Oreg.) and based upon prior instrument calibration is expressed in atmospheres. Core temperature are maintained using a homeothermic blanket available from Harvard Apparatus (South Natick, Md.). Temperature of the temporalis muscle is continuously monitored using a thermistor probe available from Physiotemp Systems (Clifton, N.J.). Halothane administration is maintained at about 1.0%.

Arterial blood samples are removed immediately preceding and at about 30 minutes following sham treatments or fluid percussion injuries for analysis of blood gases, electrolytes, pH, lactic acid, and hematocrit. Fluid percussion pressures are about 4.0 to about 5.0 atm, and typically yield moderately severe brain injuries. Cranial luer connectors are disconnected immediately following delivery of the fluid percussion pulse. Sham control rats are handled in an identical manner with the exception of the delivery of the fluid pressure pulse.

Immediately following fluid percussion injury, post-traumatic hypoxia is induced by substituting a 10% oxygen source to deliver the halothane for continued anesthesia. At the conclusion of about 30 minutes of posttraumatic hypoxia, an arterial blood sample is removed for blood gas analysis. The arterial catheters are then removed and the surgical wound sites are closed with nylon sutures and treated with the topical antibacterial furizolidine. The rats are kept warm with a Vetko thermal barrier until recovered from anesthesia (i.e. ambulatory), at which time they are returned to the operant conditioning chambers or to their home cages. In all experimental groups, at the conclusion of acute monitoring, arterial and venous catheters are removed, the surgical wound sites are closed with nylon sutures and treated with the topical antibacterial furizolidine.

The dosages of the lipoic acid compounds may be adjusted based on evaluation of initial studies. ALA will be given s.c., as per Wolz & Kriglstein (1996) Neuropharmacology 35:369–375, which is herein incorporated by reference. For example, about 50 mg/kg of ALA and about 25 mg/kg of DHLA is administered s.c. about 30 minutes after FP (immediately after the post-FP hypoxia). Follow-up doses of about 100 mg/kg of ALA and about 50 mg/kg of DHLA may be given s.c. at about 3, about 24, about 48 and about 72 hours after FP.

About 300 mg/kg of the nitrone, SPBN, is administered s.c. about 30 minutes after FP, with repeated injections s.c. about every four hours for about 72 hours. In studies examining the effects of vitamin E, about 25 mg/kg of alpha-tocopherol, are injected i.p. about 0.5, about 3, about 24, about 48 and about 72 hours after FP. About 50 μg selenium is administered i.p. whenever alpha-tocopherol is administered.

For studies evaluating prophylactic treatments, about 100 mg/kg of ALA are administered s.c. daily for three days prior to FP, followed by about 50 mg/kg s.c. one hour prior to FP. If ALA is administered only, then about 100 mg/kg of ALA are administered s.c. about 72 hours, about 48 hours, about 24 hours, about 2 hours or a combination thereof prior to FP. If coenzyme Q 10 is administered, then about 200 mg/kg of coenzyme Q 10 is administered p.o.×10 days. If SPBN is administered, about 300 mg/kg is administered s.c. q.i.d. during about 72 hours of pretreatment. If alpha-tocopherol is administered, about 25 mg/kg is injected i.p. about two hours prior to FP. About 50 micrograms i.p. of selenium may be administered when alpha-tocopherol is administered.

EXAMPLE 3

Intracerebral Injection of Ferric Chloride

Sprague-Dawley rats weighing about 200 g to about 280 g from Charles River (Wilmington, Mass.) are maintained either in hanging cages or housed separately, on 12 hour light-dark cycles with unlimited access to food and water. All procedures are performed with aseptic techniques and sterile instruments and electrodes/cannulae which are autoclaved or glass bead sterilized. Surgical procedures are performed with about 37.5 mg/kg intraperitoneal injection i.p. pentobarbital sodium anesthesia. At the time of complete insensitivity to painful stimuli, e.g. nonresponsive to tail pinch at about 20 minutes post-injection, the scalp is shaved, a surgical scrub is performed, and the rat placed in a stereotaxic frame. For stereotaxic surgery, the incisor bar is set about 3.3 mm below the intraaural line. The skull is exposed and the periosteum removed and the surface of the skull is dried and marked for electrode placement.

A. Surgical Preparation for Intracortical Injection of Ferric Chloride for Acute Seizures A burr hole is made in a location over the sensorimotor cortex, about 2mm posterior and lateral to bregma and either 300 mM iron chloride or saline is unilaterally stereotaxically injected intracortically, 2.5 mm ventral to bregma, using a 30 gauge Hamilton syringe over a period of about 2 minutes. After the Hamilton syringe is withdrawn, gelfoam (Gelfoam, Kalamazoo, Mich.) is packed into the burr hole. Extradural cortical recording electrodes are implanted to evaluate the presence or absence of seizure events (rhythmic ictal EEG). Burr holes for the EEG leads, from the transmitter, are drilled in the top of the skull, about 2 mm on either side of the midline and about 2 mm anterior to lambda. The silastic insulation on the EEG leads is removed to reveal about 5 to about 8 coils of the wire. The exposed wire is then turned about 180° in line with the remaining lead and placed sideways into the hole in the skull. The leads are then attached to the implanted electrodes with a lead connector kit or leads are continuous to the transmitter. All electrodes and leads are coated with Teflon™ except for contact points requiring conductance. A cannula may also then be placed in the right lateral ventricle if i.c.v. drug administration is planned. If an i.c.v. cannula is included, an acrylic mount is constructed to hold the cannula in place while dental acrylic is secured over set screws and the electrodes (opening around the electrodes and cannula is closed with gel foam). Otherwise, if no i.c.v. cannula is implanted, the electrode assembly is completely subcutaneous.

B. Surgical Implantation of Miniature EEG Radiotransmitter and Connection to Electrodes About a 2 cm incision is made in the midscapular area and a pocket under the skin is created with a hemostat so that the subcutaneous opening is large enough to accommodate the transmitter and coiled electrodes. A transmitter is inserted in the opening. A single channel transmitter, such as CTAF40

(Data Sciences International, St. Paul, Minn.), is used for the acute seizure study; a two-channel transmitter, such as TLIOM3-F50-EET (Data Sciences International, St. Paul, Minn.), is used for bilateral hippocampal recording electrodes in the amygdalar delayed seizure study. A sterile trocar with sleeve will be used to create a subcutaneous channel opening up to the scalp incision, and, after the trocar is removed, the transmitters are passed through the sleeve to the appropriate burrholes in the skull surface making contact with the dura and then covered with gelfoam. A small acrylic mount is constructed to cover the electrodes and a set screw in the skull for stability of the recording electrodes.

C. Surgical Placement of Amygdalar Cannula for Injection of Ferric Chloride for Induction of Delayed, Spontaneous Clonic Seizures Burr holes are made in locations appropriate for stereotaxic coordinates per atlas of Paxinos and Watson, The Rat Brain in Stereotaxic Coordinates. Academic Press, New York (1986), which is herein incorporated by reference. Coordinates for the amygdaloid body is about 3.3 mm posterior and about 5.0 mm lateral to the bregma and about 8.5 mm below the surface of the skull. A 22 gauge guide cannula, lumen occluded with stylet, is stereotaxically placed about 0.5 mm above the left amygdala. Coordinates for the dorsal hippocampus is about 3.3 mm posterior and about 1.5 mm bilateral to the bregma and about 3.4 mm below the surface of the skull. Teflon-coated stainless steel recording electrodes with less than about 0.25-mm bare tips are positioned into dorsal hippocampi bilaterally in the dorsal hippocampi to evaluate the presence or absence of seizure events (rhythmic ictal EEG). Stainless steel screws are positioned in the occipital bone to provide reference and ground contacts. All electrodes are attached to wires with pin adapters and then affixed to the skull with dental acrylic. Implantation of miniature EEG radiotransmitter, connection to electrodes and post-surgical analgesia are accomplished as described in section B.

D. Intra-surgical and Post-surgical Care

During surgery and anesthesia recovery, rats are monitored by trained personnel and maintained on heating pads having a temperature of about 37° C. to aid in the regulation of body temperature. About 0.25 to about 0.5 mg/100 g of Butorphanol tartrate (Torbugesic™, A. J. Buck, Owings Mills, Md.) is administered s.c. at the onset of surgery and thereafter for the treatment of pain as evidenced by the presence of signs of discomfort such as piloerection, hunched posture, inactivity and/or anorexia. Rats are observed until they are eating, drinking and resting in a natural position after anesthesia. Rats are individually housed in cages over receivers (RPC 1) and allowed free access to food and water and are maintained on a 12 hour/12 hour light/dark cycle.

E. Intra-amygdalar Ferric Chloride Injections for Delayed Seizures

After about 5 days of recovery the stylet is removed from the guide cannula and replaced with an injection cannula comprising a 24-gauge guide wire, the tip of which is about 0.5-mm length of fused silica (0.075 mm i.d., 0.15 mm o.d.). Freely moving animals are injected with an aqueous solution of about 1.5 $\mu$l of about 100 mM ferric chloride ($FeCl_3$) having a pH of about 2.2 at a rate of about 1 $\mu$l per minute using a microinfusion pump. Control animals are injected with about 1.5 $\mu$l of about 0.9% NaCl, with pH adjusted to about 22.

F. 24 Hour EEG and Videotape Recording

EEG determinations are initiated by placing the entire microisolator on top of the Data Sciences International (DSI) Physiotel Receiver Model RPC-1 (St. Paul, Minn.) connected to a Data Exchange Matrix (DSI, St. Paul, Minn.) and a Pentium III 733 Mhz computer using a DSI A.R.T. II System (DSI, St. Paul, Minn.) for Windows NT. EEG is acquired and stored for analysis. The transmitter is activated by swiping a magnet over the subcutaneous implantation site, and EEG recording is initiated by placing the rat over the top of an RPC-I receiver (DSI, St. Paul, Minn.).

G. EEG for Acute Intracortical Ferric Chloride

EEG is recorded only for 24 hours. Examples of epileptiform spike and spike/wave patterns are illustrated in FIGS. 3a and 3b. Specific parameters for data/statistical analysis include the number of seizure events per unit time, seizure duration or duration of rhythmic paroxysmal activity and overall slowing of electrical activity in and power spectral analysis of EEG. In the power spectral analysis, identification of a decrease in mean frequency values of the amplitude spectrum of equal to or greater than about 0.5 Hz in two or more of the following frequency bands is indicative of meaningful lesions in tested regions: $\delta$(0.5–5 Hz), $\theta$ (5–10 Hz), $\alpha$ (10–16 Hz), $\beta$ (16–48) and total (0–48). Twenty-four hour videotaping of animals will be used to verify behaviors associated with seizures identified by EEG. After about 24 hour EEG, rats are euthanized, perfused and brains removed. The area of cortical lesion is quantified by digital photographic imaging. Brains are then prepared for histological analysis as described above.

ii. EEG Recording in Delayed Seizure Model

EEG data is recorded as above on a round-the-clock basis for about 30 days after intra-amygdalar ferric chloride injection. Twenty-four hour videotaping of animals is used to verify behaviors associated with seizures identified by EEG. Behaviors are scored from review of the video images by using the criteria of set forth by Racine, R. (1972) Electroencephalogr. Clin. Neurophysiol. 32:281–294, which is herein incorporated by reference, by an observer blind to the nature of the injectate received by the animals. After about 30 days, rats are tested for memory function in the Morris water maze as described below. After behavioral testing, rats are euthanized, perfused and brains removed, sectioned and stained to ascertain amygdalar placement and identify siderosis.

H. Assessment of Pharmaceutical Interventions

For selected protective agents or combinations of agents, treatment with ALA is given s.c., as per Wolz & Kriglstein (1996) Neuropharmacology 35:369–375, which is herein incorporated by reference. In the ferric chloride-induced seizure experiments, about 100 mg/kg of ALA and about 50 mg/kg DHLA is administered s.c. about 30 minutes after ferric injection. Follow-up doses of about 100 mg/kg of ALA and about 50 mg/kg of DHLA are given s.c. at about 3, about 24, about 48 and about 72 hours after ferric chloride. About 300 mg/kg of SPBN or 150 mg/kg of PBN is administered s.c. 30 minutes after FP with repeated injections every four hours lasting for about 72 hours. In studies examining the effects of vitamin E, about 25 mg/kg of alpha-tocopherol is injected i.p. about 0.5, about 3, about 24, about 48 and about 72 hours after FP. About 50 $\mu$g of selenium is administered i.p. whenever alpha-tocopherol is administered. In all experiments vehicle-treated groups and sham-operated groups are studied which identifies any effects of the compounds tested on EEG or memory. The dosages may be adjusted as necessary.

For studies evaluating prophylactic treatments, about 100 mg/kg of ALA are administered s.c. daily for three days prior to FP, followed by about 50 mg/kg s.c. one hour prior to FP. If ALA is administered only, then about 100 mg/kg of ALA are administered s.c. about 72 hours, about 48 hours, about 24 hours, about 2 hours or a combination thereof prior to FP. If coenzyme Q 10 is administered, then about 200 mg/kg of coenzyme Q 10 is administered p.o.×10 days. About 300 mg/kg of SPBN or about 100 mg/kg of PBN is administered s.c. q.i.d. during about 72 hours of pretreatment. If alpha-tocopherol is administered, about 25 mg/kg is injected i.p. about two hours prior to FP. About 50 micrograms i.p. of selenium may be administered when alpha-tocopherol is administered.

These studies are evaluated by multi-way analysis of variance. When a significant F score is found, an a posleriori or a priori test involving a multiple comparison of means, whichever is appropriate, will be used to compare individual treatment groups.

Example 4

Spatial Memory Assessment

The Morris water maze is used to evaluate the extent to which fluid percussion injury or amygdalar ferric chloride injection impairs a rat's ability to learn the location of a submerged platform in a pool of water. During the two days that precede sham treatment or fluid percussion injury, the training on the visual recognition memory task is suspended and each rat is trained to swim to the safety of a non-visible submerged platform in a circular pool of water (26° C.). On each of these days, a rat will be placed randomly at one of four locations (north, south, east, or west) in a circular pool of water and allowed to swim for about 60 seconds. If during that time the rat locates the submerged platform, it is allowed to remain on the platform for about 10 seconds. But, if the rat fails to locate the platform, at the end of about 60 seconds, it is removed from the pool. 12 learning trials are scheduled/day with about four minute breaks between each learning trial. Similarly, water maze training is accomplished two days prior to surgery for placement of amygdalar ferric chloride cannulae.

Since injury induced motor impairments might interfere with any retention tests of maze performance, the first water-maze retention test does not occur until the $8^{th}$ post-injury day. However, daily tests of visual recognition memory are scheduled for the first seven days after fluid percussion injury. On the $8^{th}$ post-injury day, visual discrimination assessments are discontinued and five retention trials are scheduled. Retention trials are identical in every respect to pre-injury learning trials, including the location of the platform. On the $9^{th}$ day, the platform is removed and a probe trial is used to determine whether a rat's preference was controlled by location of the platform or by visibility. On days 11–14, the location of the platform is changed on successive test days.

The rat's performance during all learning and retention tests is tracked and quantified by the TSE VideoMot2 (www.TSE-Systems.de) video tracking system. For each rat, the number of entries into the four quadrants (zones) of the pool, time spent in each zone, distance traveled, swim speed, as well as latency to find the platform from the initiation of a trial is collected for each rat.

Example 5

Visual Recognition Memory Test

In the visual non-matching-to-sample experiments, rats are housed in individual test cages that contain three levers, a dot-pattern module above each lever, and a food trough below the center lever. Initially, a dot pattern is illuminated over one of the side levers and rats are trained to press the lever beneath the illuminated dot pattern. After rats learn to track the location of the dot pattern above the side levers, one of several dot-patterns is illuminated above the center lever. A press on the center lever will turn the sample pattern off and simultaneously illuminate comparison dot patterns above each of the side levers. The dot pattern above one side lever matches the (sample) pattern and the dot pattern above the other lever is different. A press on the lever beneath the comparison dot pattern that is different from the sample pattern results in the delivery of food and immediately initiates a 10 second inter-trial interval. At the end of the inter-trial interval, one of the seven dot-patterns is randomly selected for presentation as a new sample.

However, a press on the lever beneath the comparison dot pattern that matches the sample dot pattern ends the trial and after a 10 second inter-trial interval, a correction trial is initiated. The previous sample is represented as a flashing dot pattern and a press on the center lever results in the representation of the comparison stimuli that appeared on the previous trial. On a correction trial, the comparison pattern that matches the flashing sample does not flash and the probability is 0.50 that the previous sample will reappear above the same lever. After a rat's non-matching performance stabilizes, a delay of variable duration will be imposed between presentation of the sample pattern and the presentation of the comparison patterns. Prior to FP, different delays between offset of the sample and presentation of the comparison patterns will be used to determine the extent to which the passage of time or activity within the delay interfere with recall of the sample.

In all experiments, accuracy and latency data from each day's experimental session will be maintained in computer files. Standard graphic display programs are used to prepare graphs and the data from experimental and control groups are analyzed with a computer program, such as SASr, using repeated measures analysis of variance and appropriate contrast tests to identify significant group differences on recovery days. See Bauman et al., (2000) Journal of Neurotrauma 17(8):679–693, which is herein incorporated by reference.

Example 6

Neuroanatomical Evaluations

After the completion of the functional assessments described above, the rats are anesthetized with about 70 mg/kg of ketamine and about 6 mg/kg of xylazine i.m. After thoracotomy and laceration of the right atrium of the heart, rats are sequentially perfused transcardially with physiological saline which results in euthanasia by exsanguination and about a 10% formalin solution for fixation. Brains are removed and, after additional immersion fixation, paraffin-embedded Nissl-stained tissue sections are prepared.

In rats subjected to intracortical injection of ferric chloride, the area of cortical lesion are quantified by digital photographic imaging.

For rats subjected to amygdalar ferric chloride injection, alternate sections are stained with Prussian Blue, to reveal the extent and location of siderosis and cresyl violet stained sections will be examined for cavitation and gliosis in the basolateral amygdala. Placement of dorsal hippocampal electrodes are evaluated in cresyl violet stained sections through that region.

Sections from FP-injured and sham rats are examined by specifically focusing on anticipated injury-induced changes in neuronal cell numbers within the hilar region of the dentate gyrus of the hippocampus. Normal neurons are identified by he presence of nuclei with clear nucleoplasm, surrounded by cytoplasm containing Nissl substance. Hilar neuronal cell numbers are counted in six 30 micron non-adjacent sections per Lowenstein et al., (1992) J. Neuroscience 12(12):4846–4853, which is herein incorporated by reference, and compared among treatment groups in subsequent statistical analysis. In addition, other neuroanatomical hallmarks of fluid percussion injury, e.g. cortical contusion, hippocampal CA1 and CA3 neurons, may be examined, and if suitably consistent within experimental groups, are analyzed by nonparametric, e.g. blinded rater score or parametric, e.g. cell number analysis. In brains from rats subjected to FP injury, degenerative changes in the lateral geniculate nucleus are determined as reported by Bauman et al. (2000) Journal of Neurotrauma accepted pending revision, which is herein incorporated by reference.

When the probability of an F score for an overall comparison among groups is p<0.05, Dunnett's test is used for post-hoc comparisons among group means. Cell counts in the hilar region of the dentate gyrus are compared using analysis of variance. Differences among nonparametric histopathological scores are determined by means of the Kruskal-Wallis test.

Example 7

Synergistic Neuroprotective Effect

The neuroprotective effect of the lipoic acids, such as DHL, may be significantly enhanced by the co-administration of SPBN and PBN.

A. DHL and SPBN

Cultured neurons were incubated with four DHL concentrations, 3.0, 10.0, 30.0, and 100.0 micromolar of DHL, with or without 10 mM SPBN for four hours. After incubation. an oxidative insult was applied by adding 50 micromolar of $H_2O_2$ for 30 minutes after which the medium was removed and replaced with Minimum Essential Medium (MEM) (Sigma. St. Louis, Mo.). After 24 hours, the colormetric MTT assay as described above was conduced to determine amount of neuroprotection.

As shown in Table 1 below and FIG. 5, SPBN significantly increased the neuroprotective efficacy of DHL. The combination of 100 micromolar DHL and 10 mM SPBN provided almost complete protection against $H_2O_2$-induced oxidative insult.

TABLE 1

| Treatment | | % | |
|---|---|---|---|
| DHL μM | SPBN mM | Neuroprotection | n |
| 3 | 0 | 1.31 ± 5.23 | 8 |
| 3 | 10 | 10.48 ± 3.04 | 8 |
| 10 | 0 | −3.68 ± 5.14 | 8 |
| 10 | 10 | 44.51 ± 11.98*** | 8 |
| 30 | 0 | 7.04 ± 7.38 | 8 |
| 30 | 10 | 48.64 ± 6.09** | 7 |
| 100 | 0 | 28.48 ± 5.83 | 8 |
| 100 | 10 | 86.44 ± 8.44*** | 8 |

Data are depicted as means±SEM (n=7 or 8). Significance was determined by one way ANOVA and the differences between the means was assessed by the Tukey-Kramer test.p<0.005; *p<0.001.

B. DHL and PBN

Cultured neurons were incubated with four DHL concentrations, 3.0, 10.0, 30.0. and 100.0 micromolar of DHL, with or without 10 mM PBN for four hours. After incubation, an oxidative insult was applied by adding 50 micromolar of $H_2O_2$ for 30 minutes after which the medium was removed with Minimum Essential Medium (MEM) (Sigma, St. Louis, Mo.). After 24 hours, the colormetric MTT assay as described above was conduced to determine amount of neuroprotection.

As shown in Table 2 below and FIG. 6, PBN significantly increased the neuroprotective efficacy of DHL.

TABLE 2

| Treatment | | % | |
|---|---|---|---|
| DHL μM | PBN mM | Neuroprotection | n |
| 3 | 0 | −1.3 ± 7.2 | 7 |
| 3 | 10 | 20.7 ± 10.5 | 6 |
| 10 | 0 | 22.2 ± 13.6 | 8 |
| 10 | 10 | 56.9 ± 11.6 | 8 |
| 30 | 0 | 22.1 ± 9.7 | 8 |
| 30 | 10 | 87.4 ± 12.0 | 8 |
| 100 | 0 | 36.9 ± 9.6 | 8 |
| 100 | 10 | 81.6 ± 11.2 | 6 |

Data are depicted as means±SEM (n=6, 7, 8). Significance was determined by one way ANOVA and the differences between the means was assessed by the Tukey-Kramer test. p<0.005; *p<0.001.

INCORPORATION BY REFERENCE

To the extent necessary to understand or complete the disclosure of the present invention, all publications, patents, and patent applications mentioned herein are expressly incorporated by reference therein to the same extent as though each were individually so incorporated.

What is claimed is:

1. A method of treating a subject suffering from a central nervous system injury or disease selected from the group consisting of traumatic brain injury, posttraumatic epilepsy, stroke, cerebral ischemia due to traumatic brain injury, and neurodegenerative diseases comprising administering to the subject a therapeutically effective amount of at least one lipoic acid compound and at least one nitrone.

2. The method of claim 1, wherein the central nervous system injury is induced by fluid percussion, a blunt object impacting the head of the subject, an object which penetrates the head of the subject, or exposure to radiation, ionizing or iron plasma, electroconvulsive shock therapy, a nerve agent, cyanide, toxic concentrations of oxygen, central nervous system malaria, or an anti-malaria agent.

3. The method of claim 1, wherein the subject is a mammal.

4. The method of claim 3, wherein the mammal is human.

5. The method of claim 1, wherein the lipoic acid compound is alpha-lipoic acid, dihydrolipoic acid, 2-(N,N-dimethylamine) ethylamido lipoate-HCL, or the oxidized or reduced R- or S-isomers thereof.

6. The method of claim 1, wherein the composition further comprises at least one reactive oxygen species scavenger or at least one neurotrophic factor.

7. The method of claim 6, wherein the reactive oxygen species scavenger is coenzyme Q, vitamin E, vitamin C, pyruvate, melatonin, niacinamide, N-acetylcysteine, GSH, or an additional nitrone.

8. The method of claim 1, wherein the therapeutically effective amount is about 0.001 mg to about 20 mg per kg of the subject.

9. The method of claim 8, wherein the therapeutically effective amount is about 1 mg to about 10 mg per kg of the subject.

10. The method of claim 9, wherein the therapeutically effective amount is about 3 mg to about 10 mg per kg of the subject.

11. The method of claim 1, further comprising a pharmaceutically acceptable excipient.

12. The method of claim 1, wherein the composition is administered intravenously, intradermally, subcutaneously, orally, transdermally, transmucosally or rectally.

13. The method of claim 12, wherein the composition is administered intravenously.

14. The method of claim 12, wherein the composition is administered orally.

15. The method of claim 12, wherein the composition is administered subcutaneously.

16. A method of preventing or inhibiting a central nervous system injury or disease selected from the group consisting of traumatic brain injury, posttraumatic epilepsy, stroke, cerebral ischemia due to traumatic brain injury, and neurodegenerative diseases in a subject comprising administering to a subject a therapeutically effective amount of at least one lipoic acid compound and at least one nitrone.

17. The method of claim 16, wherein the central nervous system injury is induced by fluid percussion, a blunt object impacting the head of the subject, an object which penetrates the head of the subject, or exposure to radiation, ionizing or iron plasma, electroconvulsive shock therapy, a nerve agent, cyanide, toxic concentrations of oxygen, central nervous system malaria, or an anti-malaria agent.

18. The method of claim 16, wherein the lipoic acid compound is alpha-lipoic acid, dihydrolipoic acid, 2-(N,N-dimethylamine) ethylamido lipoate-HCL, or the oxidized or reduced R- or S-isomers thereof.

19. The method of claim 16, wherein the composition further comprises at least one reactive oxygen species scavenger or at least one neurotrophic factor.

20. The method of claim 19, wherein the reactive oxygen species scavenger is coenzyme Q, vitamin E, vitamin C, pyruvate, melatonin, niacinamide, N-acetylcysteine, GSH, or an additional nitrone.

21. The method of claim 16, wherein the therapeutically effective amount is about 0.001 mg to about 20 mg per kg of the subject.

22. The method of claim 21, wherein the therapeutically effective amount is about 1 mg to about 10 mg per kg of the subject.

23. The method of claim 22, wherein the therapeutically effective amount is about 3 mg to about 10 mg per kg of the subject.

24. The method of claim 16, further comprising a pharmaceutically acceptable excipient.

25. The method of claim 16, wherein the composition is administered intravenously, intradermally, subcutaneously, orally, transdermally, transmucosally or rectally.

26. The method of claim 25, wherein the composition is administered intravenously.

27. The method of claim 25, wherein the composition is administered orally.

28. The method of claim 25, wherein the composition is administered subcutaneously.

29. A method of preventing, inhibiting or treating a central nervous system injury or disease selected from the group consisting of traumatic brain injury, posttraumatic epilepsy, stroke, cerebral ischemia due to traumatic brain injury, and neurodegenerative diseases, neurotoxicity or memory deficit in a subject comprising administering to the subject a therapeutically effective amount of at least one lipoic acid compound and at least one nitrone.

30. The method of claim 29, wherein the lipoic acid compound is alpha-lipoic acid, dihydrolipoic acid, 2-(N,N-dimethylamine) ethylamido lipoate-HCL, or the oxidized or reduced R- or S-isomers thereof.

31. The method of claim 29, wherein the composition further comprises at least one reactive oxygen species scavenger or at least one neurotrophic factor.

32. The method of claim 31, wherein the reactive oxygen species scavenger is coenzyme Q, vitamin E, vitamin C, pyruvate, melatonin, niacinamide, N-acetylcysteine, GSH, or an additional nitrone.

33. The method of claim 29, wherein the lipoic acid compound is administered before the central nervous system injury or disease, neurotoxicity or memory deficit.

34. The method of claim 29, wherein the lipoic acid compound is administered after the central nervous system injury or disease, neurotoxicity or memory deficit.

* * * * *